United States Patent
Tam et al.

(10) Patent No.: US 9,834,872 B2
(45) Date of Patent: *Dec. 5, 2017

(54) HIGH STRENGTH SMALL DIAMETER FISHING LINE

(71) Applicant: HONEYWELL INTERNATIONAL INC., Morristown, NJ (US)

(72) Inventors: Thomas Tam, Chesterfield, VA (US); Huy Xuan Nguyen, Midlothian, VA (US); Lori L. Wagner, Richmond, VA (US); Mark Tallent, Midlothian, VA (US); Christopher B. Miller, Glen Allen, VA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 501 days.

This patent is subject to a terminal disclaimer.

(21) Appl. No.: 14/526,701

(22) Filed: Oct. 29, 2014

(65) Prior Publication Data

US 2016/0122918 A1    May 5, 2016

(51) Int. Cl.
*D04C 1/12*     (2006.01)
*A01K 91/00*    (2006.01)

(52) U.S. Cl.
CPC .............. *D04C 1/12* (2013.01); *A01K 91/00* (2013.01)

(58) Field of Classification Search
CPC ................................. D04C 1/12; A01K 91/00
See application file for complete search history.

(56) References Cited

U.S. PATENT DOCUMENTS

| | | |
|---|---|---|
| 3,979,106 A | 9/1976 | Jaques |
| 4,321,854 A * | 3/1982 | Foote ................. A01K 91/00 43/44.98 |
| 5,659,994 A | 8/1997 | Cutter et al. |
| 5,749,214 A * | 5/1998 | Cook ................. B29C 55/065 264/290.5 |
| 5,829,979 A * | 11/1998 | Kobashigawa .... A61C 13/0003 433/180 |
| 5,881,492 A | 3/1999 | Abiru et al. |
| 6,148,597 A | 11/2000 | Cook |
| 6,434,879 B1 | 8/2002 | Safwat et al. |
| 6,575,072 B2 | 6/2003 | Pellerin |
| 7,081,298 B2 | 7/2006 | Nakanishi |
| 7,235,285 B2 | 6/2007 | Nomura |
| 7,789,007 B2 | 9/2010 | Bosman |
| 7,823,496 B2 | 11/2010 | Bosman et al. |
| 8,022,171 B2 | 9/2011 | Goossens et al. |
| 8,181,438 B2 | 5/2012 | Cook et al. |
| 8,695,317 B2 | 4/2014 | Erlendsson et al. |
| 8,752,361 B2 | 6/2014 | Smeets et al. |
| 2004/0199208 A1 | 10/2004 | Foerster |
| 2004/0267313 A1 * | 12/2004 | Amery ............ A61B 17/06166 606/228 |

(Continued)

OTHER PUBLICATIONS http://floridasportfishing.com/301b-challenge/ (Sep. 15, 2010).*

*Primary Examiner* — Shaun R Hurley

(74) *Attorney, Agent, or Firm* — Roberts & Roberts, LLP; Richard S. Roberts, Jr.

(57) ABSTRACT

Elongated bodies made from high tenacity polyolefin fibers are provided that are useful as fishing lines, and processes for making the lines. Fibers having tenacities of at least 39 g/denier are braided and fused together to form braided bodies having very small diameters.

19 Claims, 3 Drawing Sheets

(56) References Cited

U.S. PATENT DOCUMENTS

| | | |
|---|---|---|
| 2007/0135840 A1 | 6/2007 | Schmieding |
| 2008/0009903 A1* | 1/2008 | Schmieding ............ A61L 17/04 |
| | | 606/228 |
| 2008/0021501 A1 | 1/2008 | Schmieding |
| 2008/0022582 A1 | 1/2008 | Hamano et al. |
| 2008/0051834 A1* | 2/2008 | Mazzocca ............... A61L 17/04 |
| | | 606/222 |
| 2009/0158563 A1 | 6/2009 | Nakanishi |
| 2010/0098948 A1 | 4/2010 | Nakanishi |
| 2010/0192758 A1 | 8/2010 | Clough |
| 2010/0293833 A1 | 11/2010 | Bossone, III |
| 2011/0173873 A1 | 7/2011 | Nakanishi |
| 2011/0197564 A1 | 8/2011 | Zachariades |
| 2012/0021216 A1 | 1/2012 | Veillat et al. |
| 2012/0090289 A1* | 4/2012 | Cook ..................... A01K 91/00 |
| | | 57/255 |
| 2012/0198808 A1 | 8/2012 | Bosman et al. |
| 2012/0259360 A1 | 10/2012 | Mazzocca et al. |
| 2012/0285074 A1 | 11/2012 | Yang |
| 2013/0205742 A1 | 8/2013 | Smeets et al. |
| 2013/0205979 A1 | 8/2013 | Nelis et al. |
| 2013/0247534 A1 | 9/2013 | Canedo Duarte Da Rocha |
| 2014/0223799 A1 | 8/2014 | Bossone, III |
| 2015/0247269 A1* | 9/2015 | Fukushima ............ A01K 91/00 |
| | | 87/8 |
| 2016/0122918 A1* | 5/2016 | Tam ....................... A01K 91/00 |
| | | 87/8 |

\* cited by examiner 0.60 mm Diameter Braid    5.0kV x25    500µm

All 37.5 g/d UHMW PE Fibers    5.0kV x12    1000µm 0.48 mm Diameter Braid     5.0kV x25     500μm All 43.5 g/d UHMW PE Fibers     5.0kV x12     1000μm

HIGH STRENGTH SMALL DIAMETER FISHING LINE

BACKGROUND

Technical Field

This technology relates to fishing lines made from high tenacity polyolefin fibers and processes for making the lines.

Description of the Related Art

Fibers formed from ultra high molecular weight polyethylene (UHMW PE) are known to possess excellent tensile properties such as tenacity, tensile modulus and energy-to-break. Such high tenacity fibers are typically made by a "gel spinning" process, also referred to as "solution spinning." In this type of process, a solution of ultra high molecular weight polyethylene (UHMW PE) and a solvent is formed, followed by extruding the solution through a multi-orifice spinneret to form solution filaments, cooling the solution filaments into gel filaments, and extracting the solvent to form dry filaments. These dry filaments are grouped into bundles which are referred to in the art as either "fibers" or "yarns." The fibers/yarns are then stretched (drawn) up to a maximum drawing capacity to increase their tenacity.

The preparation of high strength polyethylene filaments and/or multi-filament fibers/yarns has been described for example in U.S. Pat. Nos. 4,411,854; 4,413,110; 4,422,993; 4,430,383; 4,436,689; 4,455,273; 4,536,536; 4,545,950; 4,551,296; 4,584,347; 4,663,101; 5,248,471; 5,578,374; 5,736,244; 5,741,451; 5,972,498; 6,448,359, 6,969,553; 7,078,097; 7,078,099; 7,081,297; 7,115,318; 7,344,668; 7,638,191; 7,674,409; 7,736,561; 7,846,363; 8,070,998; 8,361,366; 8,444,898; 8,506,864; and 8,747,715. Each of these inventions provides incremental improvements in UHMW PE processing technology and illustrates the great difficulty in improving the tensile properties of UHMW PE fibers. For example, while the tenacity and tensile modulus of UHMW PE fibers are increased by stretching (drawing) the fibers, they can only be stretched to a certain extent without breaking. The maximum amount that a fiber can be stretched, and thus the maximum tenacity that can be achieved for a particular fiber type, depends on several factors, including both improved raw materials and processing capabilities.

To maximize fiber tenacity, the polyethylene solution and its precursors (i.e. the polymer and solvent forming the solution) must have certain properties, such as a high intrinsic viscosity ("IV"), and must be made in a particular manner. For example, U.S. Pat. No. 8,444,898 teaches processes for producing high tenacity fibers by a specialized process that requires first forming a polyethylene solution by: a) forming a slurry of UHMW PO particles in a solvent; b) processing the slurry through an extruder at a throughput rate of at least the quantity 2.5 $D^2$ (2.5×D×D) grams per minute, where D represents the screw diameter of said extruder in centimeters, to form a non-solution mixture in the extruder wherein the mixture contains domains of molten polymer and solvent having sizes of microscopic dimensions; c) discharging said non-solution mixture from the extruder; and d) passing said mixture through a heated vessel which provides the necessary residence time to convert the mixture to a homogeneous solution of UHMW PO dissolved in the solvent. This process is distinguished from a method where a homogenous solution is formed in the extruder, because the extruder exerts a shear stress upon the mixture that reduces the maximum achievable fiber tenacity. The thus formed solution is then passed through a shaping orifice to form a molded solution article, which is then stretched and cooled to obtain a molded gel article. The molded gel article is then stretched, followed by removing the solvent from the molded gel article to form a solid fiber, with additional stretching of the fiber being performed to increase the tenacity of the fiber to 40 g/denier or more.

U.S. Pat. No. 8,747,715 teaches a process for producing high tenacity polyethylene yarns wherein fibers are highly oriented to form a product having a tenacity of greater than about 45 g/d and a tensile modulus of greater than about 1400 g/d. The process involves passing a solution of ultra high molecular weight polyethylene in a solvent through a spinneret to form a solution yarn; drawing the solution yarn that issues from the spinneret to form a drawn solution yarn; cooling the drawn solution yarn to form a gel yarn; drawing the gel yarn; removing the solvent from the gel yarn to form a dry yarn; drawing the dry yarn to form a partially oriented yarn having an intrinsic viscosity of greater than about 19 dl/g; and drawing the partially oriented yarn to form a highly oriented yarn product having a tenacity of greater than about 45 g/d and a modulus of greater than about 1400 g/d. These are just two methods that exemplify the significant investment in science and technology that goes into even incremental improvements in the tensile properties of polyethylene fibers.

These processes produce fibers, commercially available from Honeywell International Inc. of Morristown, N.J. under the trademark SPECTRA®, that ounce-for-ounce are fifteen times stronger than steel while also light enough to float on water. Due to this excellent strength to weight ratio, SPECTRA® fibers are highly desirable for the manufacture products requiring impact absorption and ballistic resistance such as body armor, helmets, breast plates and spall shields, as well as composite sports equipment. They have also been used in other non-impact related applications, such as fishing lines, with commercial success.

Fishing lines comprising multifilament gel spun polyethylene fibers are typically made by braiding together a plurality of fibers. These multi-fiber, multi-filament fishing lines have superior strength compared to monofilament fishing lines formed from other polymers, such as polyesters or nylons, so they have a lower tendency to break during use. Due to their superior strength, braided fishing lines may be fabricated with lower line diameters relative to monofilament fishing lines having the same strength. This is significant, for example, because thinner lines allow anglers to cast longer and load more line onto their rod spool compared to monofilament lines. Braided fishing lines are also preferable because they are more durable than monofilament lines and thus will last longer without breaking down due to the sun or heavy use, and they have less of a tendency to coil and tangle than monofilament line. Furthermore, the braided, multi-fiber, multifilament construction is preferable to monofilament fishing lines because the monofilament line types have a tendency to stretch during use, whereas the braided lines do not stretch or have very little stretch. In this regard, non-stretching or low stretch lines are often preferred over greater stretch lines because they give anglers a better feel when they have a bite on their hook and they make it easier to set the hook after a bite.

Despite the existing high performance of braided fishing lines, there is an ongoing need for products having improved properties and performance. In particular, there is an ongoing need in the art for braided lines having lower diameters without sacrificing line strength. The present technology provides a solution to this need in the art, converting the very high tenacity SPECTRA® fibers, such as those manufactured according to processes described in U.S. Pat. Nos.

8,444,898 and 8,747,715, into high performance fishing lines having a greater breaking strength to diameter ratio than any other fishing line heretofore known in the art.

SUMMARY

Provided is an elongate body comprising a plurality of fibers, wherein said fibers are braided together and form a braided body, wherein at least one of said fibers forming the braided body comprises an ultrahigh molecular weight polyolefin fiber having a tenacity of at least 39 g/denier.

Also provided is a method of making an elongate body comprising the steps of:

a) providing a plurality of polymeric fibers, wherein at least one of the polymeric fibers comprises an ultrahigh molecular weight polyolefin fiber having a tenacity of at least 39 g/denier;

b) optionally coating at least a portion of each fiber with either a thermoplastic resin or an oil;

c) optionally twisting or entangling the fibers;

d) braiding the polymeric fibers together to form a braided body;

e) optionally stretching said braided body, wherein the braided body is optionally heated during and/or before stretching to a temperature below the melting point of the fibers; and f) optionally fusing together the fibers forming the braided body.

Further provided is a method of making an elongate body comprising the steps of:

a) providing a plurality of fibers, wherein at least one fiber comprises an ultrahigh molecular weight polyolefin fiber having a tenacity of at least 39 g/denier;

b) optionally coating at least a portion of each fiber with either a thermoplastic resin or an oil;

c) optionally twisting or entangling the fibers;

d) braiding the plurality of fibers around a core fiber, thereby forming a braided body around the core fiber;

e) optionally stretching said braided body and core fiber, wherein the braided body and core fiber are optionally heated during and/or before stretching; and f) optionally fusing together the fibers forming the braided body.

DETAILED DESCRIPTION

Figure 1A:
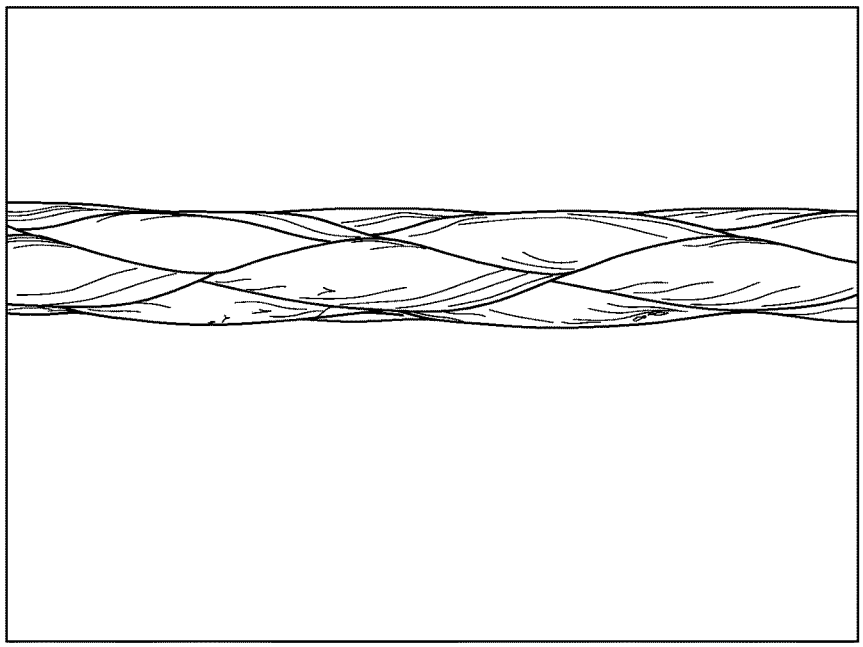
FIG. 1(A) is a scanning electron microscope (SEM) image of a prior art fishing line rated at 80 lbs. and having a line diameter of 0.6 mm, which was fabricated with ultra high molecular weight polyethylene fibers having a tenacity of 37.5 g/denier.

Provided herein are elongate bodies that are particularly suitable for use as fishing lines, though they may be used for any purpose. As used herein, "elongate bodies" are broadly defined as structures having a length dimension that is much greater than the transverse dimensions of width and thickness. As used herein, the term "fishing line" is not intended to be limiting and only indicates a potential use of the elongate bodies.

The elongate bodies comprise, consist essentially of or consist of a braided body, and all of the elongate bodies and braided bodies provided herein are formed from one or more fibers. As used herein, a "fiber" is a long strand of a material, such as a strand of a polymeric material, the length dimension of which is much greater than the transverse dimensions of width and thickness. The fiber is preferably a long, continuous strand rather than a short segment of a strand referred to in the art as a "staple" or "staple fiber." A "strand" by its ordinary definition is a single, thin length of something, such as a thread or fiber. The cross-sections of fibers for use herein may vary widely, and they may be circular, flat or oblong in cross-section. They also may be of irregular or regular multi-lobal cross-section having one or more regular or irregular lobes projecting from the linear or longitudinal axis of the filament. Thus the term "fiber" includes filaments, ribbons, strips and the like having regular or irregular cross-section. It is preferred that the fibers have a substantially circular cross-section. A single fiber may be formed from just one filament or from multiple filaments. A fiber formed from just one filament is referred to herein as either a "single-filament" fiber or a "monofilament" fiber, and a fiber formed from a plurality of filaments is referred to herein as a "multifilament" fiber. Multifilament fibers as defined herein preferably include from 2 to about 3000 filaments, more preferably from 2 to 1000 filaments, still more preferably from 30 to 500 filaments, still more preferably from 40 to 500 filaments, still more preferably from about 40 filaments to about 240 filaments and most preferably from about 120 to about 240 filaments. Multifilament fibers are also often referred to in the art as fiber bundles or a bundle of filaments. As used herein, the term "yarn" is defined as a single strand consisting of multiple filaments and is used interchangeably with "multifilament fiber." The term "tenacity" refers to the tensile stress expressed as force (grams) per unit linear density (denier) of an unstressed specimen. The term "tensile modulus" refers to the ratio of the change in tenacity, expressed in grams-force per denier (g/d) to the change in strain, expressed as a fraction of the original fiber/tape length (in/in).

In one embodiment of the invention, the elongate bodies consist or consist essentially of a braided body such that the elongate body and the braided body are one and the same. In another embodiment, the elongate bodies may be formed wherein they further incorporate one or more a core fibers, wherein the braided body surrounds the core fiber(s) as a sheath.

Core-sheath braided constructions are conventionally known in both fishing line and rope applications. Suitable core fibers non-exclusively include any stretchable synthetic fiber, regenerated fiber or metal fiber, and may optionally also include ceramic or glass fibers. Particularly suitable core fibers for use in fishing line applications are stretchable thermoplastic fibers, including polyolefin fibers, polyester fibers and fluororesin fibers. When forming a core-sheath elongate body construction herein, the braided body may be formed around the core with the core as a central axis using conventional equipment, such as braiding machines available from Herzog Maschinenfabrik GmbH of Oldenberg, Germany, and using any conventionally known method, such as plaiting or other braid constructions, as well as a double braid technique where the core "fiber" itself is a braided structure. In this embodiment, the braided sheath structure preferably incorporates from 1 to 12 discrete fibers, more preferably from 2 to 8, still more preferably from 2 to 6, still more preferably from 2 to 4, still more preferably from 4 to 8 and most preferably from 4 to 6 discrete fibers. However, more than 12 discrete fibers may be incorporated, such as 2-20 or more, 2-30 or more, 2-40 or more, 2-50 or more, or greater than 50 discrete fibers, such as 50-100 discrete fibers. Also, rather than small diameter fishing lines, large diameter ropes may be formed that include thousands of discrete fibers, such as from 5000-6000 discrete fibers or more.

In a core-sheath construction, the braided fibers and the core are optionally fused together. Fusion of the braided fibers with the core is typically accomplished with the application of heat and tension, optionally with the application of a solvent or plasticizing material prior to exposure to heat and tension as described in U.S. Pat. Nos. 5,540,990; 5,749,214; and 6,148,597, the disclosures of which are hereby incorporated by reference to the extent consistent herewith. As described in these patents, the braided body is subjected to stretching at an elevated temperature that is within the melting point range of the filament polymer material and for a time that is sufficient to soften the filaments and to at least partially fuse together the contact surfaces of the individual filaments forming the fiber into a line having monofilament-like characteristics.

Fusion may also be accomplished by bonding, for example, by at least partially coating the fibers of the sheath and/or core with a thermoplastic resin or other polymeric binder material having adhesive properties. Suitable thermoplastic resins non-exclusively include polyolefin resins such as polyolefin wax, low density polyethylene, linear low density polyethylene, polyolefin copolymers, ethylene copolymers such as ethylene-acrylic acid copolymer, ethylene-ethyl acrylate copolymer, ethylene-vinyl acetate copolymer, polyisoprene-polystyrene-block copolymers (such as KRATON® D1107 commercially available from Kraton Polymers of Houston, Tex.), polyurethanes, polyvinylidene fluoride, polychlorotetrafluoroethylene (PCTFE), and copolymers and blends of one or more of the foregoing. Suitable polyolefin waxes non-exclusively include ACumist® micronized polyolefin waxes commercially available from Honeywell International Inc. of Morristown, N.J. The most preferred thermoplastic resin will have a lower melting point than the specific polyolefin fiber that is utilized and is a drawable material, and most preferably is a polyolefin resin. The fibers of the braided body sheath may also be thermally bonded together and/or to the core fiber without an adhesive coating. Thermal bonding conditions will depend on the fiber types. The fibers may also be pre-coated with an oil prior to fusing, such as mineral oil, paraffin oil or vegetable oil as is conventionally known in the art, such as is described in U.S. Pat. Nos. 5,540,990; 5,749,214; and 6,148,597. As stated in said patents, mineral oil acts as a plasticizer that enhances the efficiency of the fusion process permitting the fusion process to be performed at lower temperatures. Any conventional method may be used to coat the fibers with the oil or thermoplastic resin, such as dipping, spraying or otherwise passing the fibers through bath of the coating material.

When the fibers of the sheath and/or the core are coated with a resin or other polymeric binder material having adhesive properties to bond the fibers together, only a small amount of the resin/binder is needed. In this regard, the quantity of resin/binder applied is typically no more than 5% by weight based on the total weight of the fibers plus the resin/binder, such that the fibers comprise at least 95% by weight of the coated fibers based on the total weight of the fibers plus the resin/binder. Accordingly, the elongate body will comprise at least 95% by weight of the component fibers. In more preferred embodiments, the elongate bodies comprise at least about 96% fiber by weight, still more preferably 97% fiber by weight, still more preferably 98% fiber by weight, and still more preferably 99% fiber by weight. Most preferably, the elongate bodies are completely resin-free, i.e. are not coated with any bonding resin/binder and consist essentially of or consist of fibers/filaments.

In the most preferred embodiments herein, the elongate bodies consist or consist essentially of the braided body without incorporating a core fiber, such that the elongate body and the braided body are one and the same, and such that braided body is essentially a braided rope of any diameter that includes no unbraided fibers or strands. The braided bodies are preferably round, having a round, circular or oval cross section, rather than flat and may be formed using any conventionally known braiding technique as would be determined by one skilled in the art, such as plaiting, single braid, solid braid or hollow braid techniques. These braided bodies where no core fiber is present are made with conventional braiding equipment and methods. Suitable braiding equipment is commercially available, for example, from Herzog Maschinenfabrik GmbH of Oldenberg, Germany.

Preferably, the braided bodies incorporate from 1 to about 12 discrete fibers, more preferably from 1 to 12 discrete fibers, more preferably from 3 to 8, still more preferably from 3 to 6, still more preferably from 3 to 4, still more preferably from 4 to 8 and most preferably from 4 to 6 discrete fibers. However, more than 12 discrete fibers may be incorporated, such as 3-20 or more, 3-30 or more, 3-40 or more, 3-50 or more, or greater than 50 discrete fibers, such as 50-100 discrete fibers. For example, ropes may include thousands of discrete fibers, such as about 5000-6000 discrete fibers or more. In this regard, the braided bodies may be useful in many other embodiments beyond fishing lines, such as sash cords, water ski ropes, mountaineering ropes, yachting ropes, parachute lines, fishing nets, mooring lines, hawsers, shoe laces, medical applications such as catheters or dental floss, high-pressure tubes, ground cables and harnesses.

Similar to the core-sheath fibers discussed above, the fibers forming these single braided, solid braided or hollow bodies may optionally be fused together according to the techniques described above from U.S. Pat. Nos. 5,540,990; 5,749,214; and 6,148,597, wherein the individual fibers forming the braided body are fused together optionally with the application of heat and tension. When this option is performed, the braided body is optionally subjected to stretching, optionally at an elevated temperature that is within the melting point range of the filament polymer material that is sufficient to at least partially fuse the contact surfaces of the individual filaments forming the fiber into a line having monofilament-like characteristics. Conditions useful for the stretching/surface fusion process are the same as recited above for core-sheath fibers. The fibers forming the braided bodies may also be at least partially coated with either a thermoplastic resin or an oil followed by fusing them together as noted above. Suitable thermoplastic resins, waxes and oils are the same as those described above.

However, in the most preferred embodiments, the fibers forming the braided body are not fused together, i.e. they are unfused. This is distinguished from the method of U.S. Pat. Nos. 5,540,990; 5,749,214; and 6,148,597 where the fibers are fused together. In this regard, the braided body may be stretched or unstretched, although it is preferably stretched, and stretching may be performed with or without heating the fibers/braided body, although heating is preferred. As described herein, stretching of the braided body refers to stretching after braiding the fibers together into the braided body, wherein even in an unstretched braided body, the component fibers forming the braided body are almost always stretched prior to braiding during the gel/solution spinning process in order to enhance their tenacity, as described in commonly owned U.S. Pat. Nos. 7,846,363; 8,361,366; 8,444,898; 8,747,715 and U.S. publication no. 2011-0269359 discussed below. When it is desired to stretch the braided body with heat but without fusing the component fibers of the braid, fusing is avoided by heating the braided body to a temperature below the melting point of the fibers. For example, when the braided body incorporates ultra high molecular weight, gel spun polyethylene multifilament fibers, this temperature is preferably within the range of from about 145° C. to about 153° C., more preferably from about 148° C. to about 151° C. In this regard, it is noted that highly oriented, ultra high molecular weight polyethylene fibers generally have a higher melting point than bulk UHMW PE or lower molecular weight polyethylenes. During this stretching without fusion process, the fiber is preferably held under tension that is preferably applied continuously. Preferably, the stretching step without fusion is conducted at an overall stretching ratio in one or more stages of stretching of from about 1.01 to about 3.0, and more preferably from about 1.1 to about 1.8, preferably with the application of heat.

In the braided bodies described herein, the greater the braid density, the more monofilament-like characteristics the braids will have, which is particularly relevant in fishing line applications. In this regard, the point at which braided fibers cross one another is called a "pick" and braid tightness, also referred to as braid density, is measured in "picks per inch" ("PPI"). The distance between each pick is referred to in the art as the "pitch" of the braid. The braid density/tightness may be adjusted as desired using the selected equipment to increase or decrease the number of picks along the length of the braid. In the preferred embodiments, the braided body has a density of less than about 25 PPI or from about 0.5 PPI to about 25 PPI, more preferably a density of less than or equal to 20 PPI or from about 0.5 PPI to 20 PPI, more preferably from about 14 picks per inch to about 20 picks per inch, still more preferably from about 14 picks per inch to about 20 picks per inch, still more preferably from 15 PPI to 19 PPI, still more preferably greater than 15 PPI to less than 20 PPI, and most preferably from 17 PPI to 19 PPI in length of the braided body. Each of these ranges are specific to the braid density/tightness of unstretched braided bodies, i.e. the braided bodies after braiding but before any optional additional stretching of the braided bodies.

It is generally known that increases in braid density result in a corresponding loss in braid tenacity. However, it has been unexpectedly found that the braided bodies provided herein uniquely do not decrease in tenacity at certain densities. It has been observed that at braid densities greater than 15 PPI but less than or equal to 20 PPI, particularly at 17-19 PPI, the braided bodies do not decrease in tenacity. As a result, the braided bodies provided herein take advantage of the benefits of high braid density without sacrificing tenacity. This imparts more monofilament-like characteristics and performance to the braided body. For fishing lines particularly, such benefits include improved casting-ability, reduced casting noise and higher durability.

All fibers useful herein for forming the elongate bodies/braided bodies are preferably polymeric fibers, most preferably thermoplastic polymer fibers formed from one or more thermoplastic polymers. In each of the embodiments of the invention, at least one of said fibers forming the braided body comprises an ultrahigh molecular weight polyolefin fiber having a tenacity of at least 39 g/denier. Said fibers preferably have a tenacity of from about 39 g/denier to about 70 g/denier, or at least 40 g/denier. The most preferred polyolefin fibers are polyethylene fibers, most preferably gel spun (solution spun) ultra high molecular weight polyethylene fibers having a tenacity of at least 39 g/denier. More preferably, the polyethylene fibers have a tenacity of from about 43 g/denier to about 70 g/denier, still more preferably have a tenacity of 43 g/denier or more, or at least 43.5 g/denier, still more preferably from about 45 g/denier to about 70 g/denier, still more preferably have a tenacity of at least 45 g/denier, at least about 48 g/denier, at least about 50 g/denier, at least about 55 g/denier or at least about 60 g/denier. Additionally, polyethylene fibers useful for forming the braided body can have a tensile modulus greater than about 1400 g/d, including up to about 2000 g/d, or greater than about 2000 g/d.

As stated above, to manufacture high tenacity polyolefin fibers, the polyolefin polymer raw material must have a high molecular weight and a high intrinsic viscosity. High molecular weight, high IV polymers will yield high IV fibers having high tenacity. Ultra high molecular weight polyethylene filaments, fibers and yarns in particular are formed from extended chain polyethylenes having molecular weights of at least 300,000, preferably at least one million and more preferably between two million and five million. The most preferred UHMW PE fibers have an intrinsic viscosity when measured in decalin at 135° C. by ASTM D1601-99 of greater than about 19 dl/g to about 40 dl/g, preferably at least about 20 dl/g to about 40 dl/g, more preferably from about 22 dl/g to about 40 dl/g, and most preferably from about 25 dl/g to 40 dl/g. Processing of the fibers will reduce the intrinsic viscosity of the polymer to a degree, so the UHMW PE raw material must have a greater IV than the final product. As described in U.S. Pat. No. 8,747,715, the UHME PE that is selected for use in the gel spinning process can have an intrinsic viscosity in decalin at 135° C. of at least about 30 dl/g, or greater than about 30 dl/g, including being from about 30 dl/g to about 100 dl/g, or greater than about 100 dl/g. In some examples, the UHMW PE can have an intrinsic viscosity in decalin at 135° C. of about 30 dl/g, about 35 dl/g, about 40 dl/g, about 45 dl/g, about 50 dl/g, about 55 dl/g, about 60 dl/g, about 65 dl/g, about 80 dl/g, about 85 dl/g, about 90 dl/g, about 95 dl/g, or about 100 dl/g. The preferred UHMW PE polymer IV ranges from about 30 dl/g to about 50 dl/g. Further, in at least some examples, highly oriented UHMW PE fibers useful herein have an intrinsic viscosity that is from about 0.2 times the intrinsic viscosity of the UHMW PE polymer from which the fiber was made to about 0.65 times the intrinsic viscosity of the UHMW PE polymer from which the fiber was made.

The most preferred UHMW PE fibers also are highly oriented and have a c-axis orientation function of at least about 0.96, preferably at least about 0.97, more preferably at least about 0.98 and most preferably at least about 0.99. The c-axis orientation function is a description of the degree of alignment of the molecular chain direction with the filament direction. A polyethylene filament in which the molecular chain direction is perfectly aligned with the filament axis would have an orientation function of 1. C-axis orientation function ($f_c$) is measured by the wide angle x-ray diffraction method described in Correale, S. T. & Murthy, Journal of Applied Polymer Science, Vol. 101, 447-454 (2006) as applied to polyethylene.

While the braided body only need include one of such high strength polyolefin fibers, it is most preferred that all the fibers forming the braided body are polyolefin fibers possessing these properties. Most preferably, all of the fibers forming the braided body comprise, consist essentially of or consist of multifilament ultrahigh molecular weight polyethylene fibers, each having a tenacity of at least 39 g/denier, more preferably multifilament, ultra high molecular weight polyethylene fibers each of which has a tenacity of at least 43 g/denier, and most preferably, multifilament, ultra high molecular weight polyethylene fibers each of which has a tenacity of at least 45 g/denier, each preferably also possessing the other properties identified above, including a tensile modulus of at least about 1400 g/d.

Ultra high molecular weight polyolefin (UHMW PO) or UHMW PE polyethylene fibers useful herein for forming the braided bodies may be fabricated from any process that is capable of producing UHMW PE fibers having tenacities of at least 39 g/denier, most preferably where the fibers are multi-filament fibers. The most preferred processes include those described in U.S. Pat. Nos. 7,846,363; 8,361,366; 8,444,898; 8,747,715; as well as U.S. publication no. 2011-0269359, the disclosures of which are incorporated by reference herein to the extent consistent herewith.

As described in U.S. Pat. No. 8,444,898, a process is provided wherein a polyethylene solution is formed by processing an UHMW PO/solvent slurry under specialized conditions to convert it into a homogeneous solution of UHMW PO dissolved in the solvent. The thus formed solution is then passed through a shaping orifice to form a molded solution article, which is then stretched and cooled to obtain a molded gel article. The molded gel article is then stretched, followed by removing the solvent from the molded gel article to form a solid fiber, with additional stretching of the fiber being performed to increase the tenacity of the fiber.

As described in U.S. Pat. No. 8,747,715 and related U.S. publication no. 2011-0269359, a process for producing gel spun yarns made from ultra high molecular weight polyethylene is provided, the process comprising the steps of: feeding a slurry that comprises an UHMW PE and a spinning solvent to an extruder to produce a liquid mixture, the UHMW PE having an intrinsic viscosity in decalin at 135° C. of at least about 30 dl/g; passing the liquid mixture through a heated vessel to form a homogeneous solution comprising the UHMW PE and the spinning solvent; providing the solution from the heated vessel to a spinneret to form a solution yarn; drawing the solution yarn that issues from the spinneret at a draw ratio of from about 1.1:1 to about 30:1 to form a drawn solution yarn; cooling the drawn solution yarn to a temperature below the gel point of the UHMW PE polymer to form a gel yarn; drawing the gel yarn in one or more stages at a first draw ratio DR1 of from about 1.1:1 to about 30:1; drawing the gel yarn at a second draw ratio DR2; removing spinning solvent from the gel yarn in a solvent removal device to form a dry yarn; drawing the dry yarn at a third draw ratio DR3 in at least one stage to form a partially oriented yarn; transferring the partially oriented yarn to a post drawing operation; and drawing the partially oriented yarn at a post drawing temperature in the post drawing operation to a fourth draw ratio DR4 of from about 1.8:1 to about 15:1 to form a highly oriented yarn product having a tenacity of greater than about 45 g/d (40.5 g/dtex) and a modulus of greater than about 1400 g/d. As explained in this patent, the drawing conditions in each drawing step are carefully controlled, with the final drawing step being conducted in one extremely long oven or in a series of ovens, each of which is a forced hot air convection oven, as compared to in a nitrogen blanketed oven having no forced air flow. This is because the lack of forced air flow will establish a laminar flow regime with temperature differences will exist from exterior to interior filaments (in a multifilament fiber bundle that is being stretched), with the consequence of non-uniform drawing across the bundle and limited maximum draw capability. The convection oven provides a turbulent gas flow that agitates the fiber bundle, minimizing temperature differences and permitting more uniform and higher drawing.

Methods of forming polyolefin fibers having tenacities of 39 g/denier or more are also described in U.S. Pat. No. 7,846,363 and related U.S. Pat. No. 8,361,366. U.S. Pat. No. 7,846,363 describes a process for the production of a multifilament poly(alpha-olefin) yarn comprising the steps of: a) forming a solution of a poly(alpha-olefin) in a solvent at an elevated temperature, said poly(alpha-olefin) having an intrinsic viscosity when measured in decalin at 135° C. of from about 5 to about 45 dl/g; b) passing said solution through a multi-filament spinneret to form a solution yarn, said spinneret being at an elevated temperature; c) drawing said solution yarn at a draw ratio of from about 1.1:1 to about 30:1; d) rapidly cooling said solution yarn to a temperature below the gel point of said solution, to form a gel yarn; e) drawing said gel yarn in at least one stage to a first draw ratio DR1; f) removing solvents from said get yarn while drawing at a second draw ratio DR2 in at least one stage to form an essentially dry yarn containing less than about 10 weight percent of solvents; g) drawing said dry yarn to a third draw ratio DR3 of from about 1.10:1 to about 2.00:1 in at least one stage to form a partially oriented yarn; h) optionally relaxing said partially oriented yarn from about 0.5 to about 5% of its length; i) winding up said partially oriented yarn; j) unrolling said partially oriented yarn and drawing it in at least one stage at a temperature of from 130° C. to 160° C. to a fourth draw ratio DR4 of from about 1.8:1 to about 10:1 to form a highly oriented yarn having a tenacity of from about 38 to about 70 g/d (34.2 to 63 g/dtex) as measured by ASTM D2256-02 at 10 inch (25.4 cm) gauge length and a strain rate of 100%/min; k) cooling said highly oriented yarn under tension and winding it up; wherein the product of the draw ratios DR1×DR2×DR3 is greater than or equal to about 5:1, wherein the fractional off-line draw of the dry yarn (FOLDY), defined by the relationship, is from about 0.75 to about 0.95, and wherein steps a) through i) are conducted continuously in sequence and are discontinuous with continuous sequential steps j) to k). Related U.S. Pat. No. 8,361,366 provides a similar process wherein the FOLDY limitation is not required but wherein the partially oriented yarn is produced at a rate of at least about 0.35 g/min per filament of said partially oriented yarn.

Ultra high molecular weight polyolefin fibers having a tenacity of at least 39 g/denier, particularly those fabricated according to the methods described in U.S. Pat. Nos. 7,846,363; 8,361,366; 8,444,898; 8,747,715; and U.S. publication no. 2011-0269359 have been unexpectedly found to produce fibers having reduced thermal shrinkage at elevated temperatures relative to fibers having tenacities below 39 g/denier, such as 37.5 g/denier, particularly those produced by other processes. As a result of the reduced fiber thermal shrinkage, the thermal shrinkage of the braided bodies formed from these fibers is correspondingly reduced, resulting in fishing lines having unexpectedly improved durability and resistance to degradation due to heat and sunlight.

As used herein, "thermal shrinkage" refers to shrinkage observed due to increased temperatures, and it may be measured in terms of the percent decrease in length that is observed under a given temperature. Thermal shrinkage of the braided body is determined herein by the ASTM D4974 "Hot Air Thermal Shrinkage of Yarn and Cord Using a Thermal Shrinkage Oven" method. This method measures thermal shrinkage at 177° C. and accordingly is intended for use with fibers/yarns made from nylon, polyester, and other polymers not detrimentally affected by that temperature. The method may be used with other polymer types at other temperatures, and for the polyethylene fibers used herein which melt at a temperature ranging from about 150° C.–155° C., testing was performed at 145° C. In accordance with the present disclosure, the braided bodies preferably have a thermal shrinkage property in 2 minutes at 145° C. as determined by ASTM D4974-99 of 3.0% or less, more preferably less than 3.0%, still more preferably 2.5% or less, still more preferably less than 2.5%, still more preferably 2.3% or less, still more preferably less than 2.3%, still more preferably 2.15% or less, still more preferably less than 2.15%, still more preferably 2.0% or less, and most preferably less than 2.0%. The thermal shrinkage amount of the most preferred braided bodies, where the fibers forming the braided body are exclusively UHMW PE fibers, in 2 minutes at 145° C. can be expressed by the equation 0.2242 (PPI)–2.209+b, wherein PPI is greater than 15 but less than 20, and wherein b is greater than −0.1.

These most preferred UHMW PE fibers have also been found to achieve braided bodies having a low creep tendency. As is conventionally known, "creep" is the long-term, longitudinal deformation of a material over time when subjected to a continuing load. The creep tendency of an elongate body, such as a fiber, yarn or braided body may be determined, for example, by subjecting a sample to a selected sustained load (e.g. 10% of the breaking strength of the test specimen) over a selected time (e.g. 300 minutes for short term creep, or 10,000 minutes for long term creep) at a selected temperature (e.g. room temperature, such as 70-72° F., or heated to 70° C.) whereby the elongation of the sample is measured after the selected time expires. In this method, the creep percentage may be calculated according to the following equation that is outlined in U.S. Pat. No. 5,578,374, the disclosure of which is incorporated by reference herein to the extent consistent herewith:

$$\% \text{ creep} = 100 \times [A(s,t) - A(o)]/A(o)$$

where $A(o)$ is the length of the test section immediately prior to application of load, s; and where $A(s,t)$ is the length of the test section at time t after application of load, s.

As used herein, a "low creep" braided body preferably exhibits about 3.0% or less elongation, more preferably about 2.0% or less elongation, still more preferably about 1.5% or less elongation, still more preferably about 1.0% or less elongation and most preferably about 0.5% or less elongation when the braided body is subjected to a stress equal to 10% of the breaking strength of the braided body for 10,000 minutes at room temperature (approximately 70° F.–72° F.), wherein the "breaking strength" of the braided body equals the denier times (x) the ultimate tensile strength ("UTS"; also referred to herein as tenacity) of the braided body. The UTS of a fiber or of the braided body is the maximum load it can withstand before breaking. When creep is measured at 70° C. with the braided body being subjected to a stress equal to 10% of the breaking strength of the braided body for 300 minutes, the braided body preferably exhibits about 5.0% or less elongation, more preferably about 4.0% or less elongation, and most preferably about 3.0% or less elongation.

When the fibers forming the braided body are multifilament fibers rather than monofilament fibers, as is preferred, the multifilament fibers may optionally be twisted or air entangled prior to braiding. Various methods of twisting fibers are known in the art and any method may be utilized. Useful twisting methods are described, for example, in U.S. Pat. Nos. 2,961,010; 3,434,275; 4,123,893; 4,819,458 and 7,127,879, the disclosures of which are incorporated herein by reference to the extent consistent herewith. In a preferred embodiment, the fibers are twisted to have at least about 0.5 turns of twist per inch of fiber length up to about 15 twists per inch, more preferably from about 3 twists per inch to about 11 twists per inch of fiber length. In an alternate preferred embodiment, the fibers are twisted to have at least 11 twists per inch of fiber length, more preferably from about 11 twists per inch to about 15 twists per inch of fiber length. The standard method for determining twist in twisted fibers is ASTM D1423-02. Similarly, various methods of air entangling multifilament fibers are conventionally known and described, for example, in U.S. Pat. Nos. 3,983,609; 4,125,922 and 4,188,692, the disclosures of which are incorporated by reference herein to the extent consistent herewith. In a preferred embodiment, the multifilament fibers are neither twisted nor air entangled. Also, prior to braiding multiple fibers together to form the braided body, the individual fibers themselves are preferably non-braided.

It has been found that a braided body formed from a plurality of fibers wherein at least one of said fibers forming the braided body comprises an ultrahigh molecular weight polyolefin fiber having a tenacity of at least 39 g/denier, more preferably a tenacity of at least 43 g/denier, most preferably a tenacity of at least 45 g/denier, will have a braided body tenacity of at least 22 g/denier, more preferably at least 23 g/denier and most preferably at least 24 g/denier. The highest tenacities are typically achieved when all or most of the fibers of the braided body comprise ultra high molecular weight polyethylene fibers having tenacities of greater than 39 g/denier, typically at least about 43 g/denier, more typically at least about 45 g/denier. The tenacity of the braided body will be lower than the tenacities of the component fibers because the fibers in the braided body are coiled into a helix and therefore are not fully straight, which inhibits exploitation of the full tensile strength of fibers. Utilizing such high tenacity fibers beneficially produces fishing lines, ropes and other elongate bodies having improved breaking strength and knot strength relative to elongate bodies formed with lower tenacity fibers, particularly fibers having tenacities below 39 g/denier.

As noted above, the breaking strength of the braided body equals the denier times the tenacity of the braided body. In preferred embodiments, the braided body has a breaking strength of at least 83.0 pounds force (lbf), more preferably at least 85.0 lbf, and most preferably at least 87.0 lbf for unstretched braided bodies. Commercially available fishing line ratings are often marketed according to their knot strength rather than their breaking strength, and the fishing lines provided herein exhibit superior Palomar knot strength (i.e. strength of a Palomar knot) relative to prior art fishing lines. Palomar knot strength is measured according to conventionally known methods. In the preferred embodiments, the braided bodies have a Palomar knot strength of at least 50 lbf., more preferably at least 52 lbf., still more preferably at least 54 lbf., still more preferably at least 56 lbf., still more preferably at least 58 lbf., and most preferably at least about 60 lbf. or ≥60 lbf. This is reflected in the samples tested in Example 1 as outlined in Table 1 below. In a most preferred embodiment, a braided body formed exclusively from UHMW PE fibers having fiber tenacities of at least about 43.5 g/denier, wherein the braided body has a denier of at least 1500 (e.g. from 1500 to 1800) and a braid density of from 18 PPI to 19 PPI, has a Palomar knot strength of at least 60 lbf.

Figure 1B:
FIG. 1(B) is an SEM image of the fishing line of FIG. 1(A) showing that the 80 lb., 0.6 mm diameter fishing line was fabricated with six 37.5 g/denier fibers.
Figure 2A:
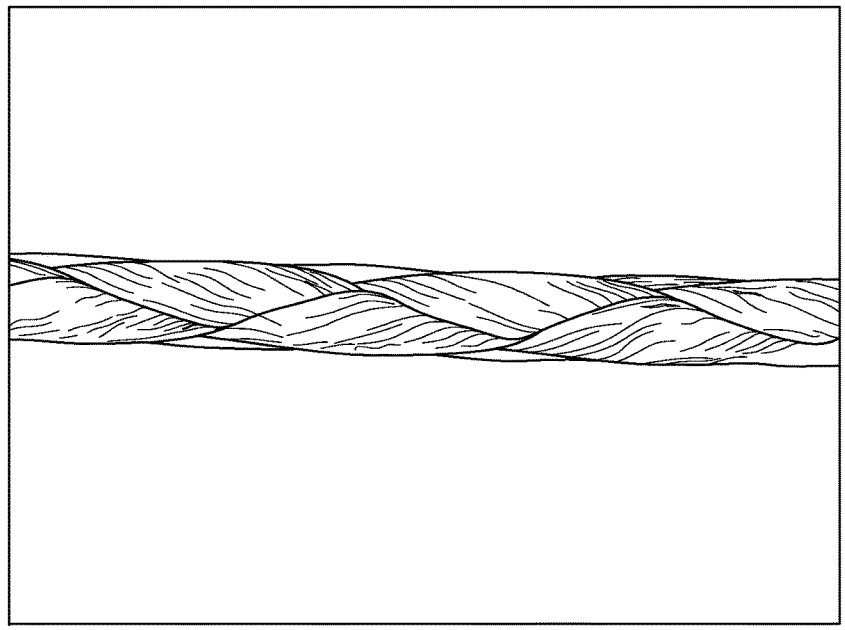
FIG. 2(A) is an SEM image of a fishing line rated at 80 lbs. and having a line diameter of 0.48 mm, which was fabricated with ultra high molecular weight polyethylene fibers having a tenacity of 45.0 g/denier.
Figure 2B:
FIG. 2(B) is an SEM image of the fishing line of FIG. 2(A) showing that the 80 lb., 0.48 mm diameter fishing line was fabricated with four 45.0 g/denier fibers.

As illustrated in FIGS. 1(A)-(B) (prior art) and FIGS. 2(A)-(B), unfused, unstretched fishing lines rated at an 80 lb. weight rating are provided herein that are fabricated with fibers having a tenacity of 43.5 g/denier are 20% thinner than fishing lines fabricated with fibers having a tenacity of 37.5 g/denier, with all other characteristics being equivalent except for the number of fibers and filaments incorporated in the braid. As seen in the photographs, a total of six unfused 37.5 g/denier fibers are required to form an elongate body meeting the 80 lb. weight rating, while comparatively, the same rating is achieved with only four unfused 43.5 g/denier fibers forming an elongate body having the same weight rating. These comparative differences are observed for all fishing line weight ratings, not only an 80 lb. rating. Accordingly, an elongate body described herein being formed from fibers having a tenacity of greater than 39 g/denier has a greater breaking strength and/or knot strength relative to a comparison elongate body having an identical diameter, wherein the comparison elongate body is equivalent to the elongate body except that all fibers forming the comparison elongate body have a tenacity of less than 39 g/denier. Further, an elongate body described herein formed from fibers having a tenacity of greater than 39 g/denier and having an identical breaking strength as a comparison elongate body that is equivalent to the elongate body except that all fibers forming the comparison elongate body have a tenacity of less than 39 g/denier, will have a significantly smaller diameter than the comparison elongate body, i.e. a diameter that is at least about 20% thinner than the comparison elongate body.

The elongate bodies and braided bodies provided herein will not have one, single fixed diameter, but can be of any diameter, which diameter will be lower than any comparison elongate body formed by braiding together the same number of lower tenacity fibers. The diameter of a fiber can be calculated from the fiber denier with the following formula:

$$\text{Diameter} = \sqrt{\frac{\text{Denier}}{9000 \cdot \text{density} \cdot 0.7855}}$$

where density is in grams per cubic centimeter (g/cm³) (g/cc) and the diameter is in mm. In this regard, the term "denier" refers to the unit of linear density equal to the mass in grams per 9000 meters of fiber. The denier of a multifilament fiber is determined by the number of filaments forming the multifilament fiber and the denier of each filament, known as denier per filament ("dpf"). In this regard, a typical, most preferred multifilament fiber will have from about 40 to about 240 individual filaments, so dividing the total fiber denier by the number of filaments gives you the dpf. Ultra high molecular weight polyethylene has a density of 0.97 g/cc, though at very high molecular weights that may increase to from about 0.98 g/cc to about 0.995 g/cc, as would be known by one skilled in the art. The denier of a braided body may also be calculated by adding together the denier of each individual fiber forming the braided body.

Generally, the lower the fiber denier, the smaller the fiber diameter, and it is typical for fibers having greater tenacities to be of a smaller diameter because high tenacity fibers are highly oriented (stretched/drawn) to increase their tenacity. In the preferred embodiments herein, multifilament fibers forming the braided body have a denier of from about 10 to about 800, more preferably from about 20 to about 600, still more preferably from about 30 to about 500, still more preferably from about 30 to about 400 and most preferably from about 30 to about 300, for a multifilament fiber having from about 40 to about 240 total filaments. The braided body itself incorporating, for example, from 3 to 12 discrete fibers without a core fiber will have a denier of from about 30 to about 2300, more preferably from about 40 to about 1900, still more preferably from about 1300 to about 1900, still more preferably from about 1000 to about 1800, still more preferably from about 1500 to about 1800 or from about 1200 to about 1750, and most preferably from about 1600 to about 1750. The braid denier will typically be greater than the combined denier of all the component fibers because due to the braid construction, where fibers are turned over each other at the crossover points, i.e. picks, 9000 meters of the braid will incorporate more than 9000 meters of each individual fiber.

Regardless the total number of filaments, fibers or strands in the elongate bodies and/or braided bodies, and notwithstanding the breaking strength of the elongate bodies and/or braided bodies, the elongate bodies and braided bodies most preferably have very small diameters as is desirable for their use as fishing lines. Preferably, the elongate bodies, and particularly the braided bodies when no core fiber is present, have a diameter of 2.0 mm or less, 1.9 mm or less, 1.8 mm or less, 1.7 mm or less, 1.6 mm or less, 1.5 mm or less, 1.4 mm or less, 1.3 mm or less, 1.2 mm or less, 1.1 mm or less, 1.0 mm or less, 0.9 mm or less, 0.8 mm or less, 0.7 mm or less, 0.6 mm or less, 0.5 mm or less, 0.4 mm or less, 0.3 mm or less, or 0.2 mm or less. These diameters are consistent with those of conventional braided fishing lines, but fishing lines as fabricated herein will have superior breaking strengths and/or knot strengths compared to said conventional braided fishing lines at identical diameters.

While the braided bodies of the most preferred embodiments are said to include only multifilament polyethylene fibers having tenacities of at least 39 g/denier, they may additionally include other polyolefin or polyethylene fibers having lower tenacities, including any fibers disclosed, for example, in U.S. Pat. Nos. 4,411,854; 4,413,110; 4,422,993; 4,430,383; 4,436,689; 4,455,273; 4,536,536; 4,545,950; 4,551,296; 4,584,347; 4,663,101; 5,248,471; 5,578,374; 5,736,244; 5,741,451; 5,972,498; 6,448,359; 6,969,553; 7,078,097; 7,078,099; 7,081,297; 7,115,318; 7,344,668; 7,638,191; 7,674,409; 7,736,561; 7,846,363; 8,070,998; 8,361,366; 8,444,898; 8,506,864; and 8,747,715, each of which is incorporated herein by reference to the extent consistent herewith. This includes all polyolefin fiber types, including polypropylene fibers, high density polyethylene and low density polyethylene fibers. The braided bodies may also include as component fibers other non-polyolefin fibers, such as conventionally known and commercially available aramid fibers, particularly para-aramid fibers and meta-aramid fibers, polyamide fibers, polyester fibers including polyethylene terephthalate fibers and polyethylene naphthalate fibers, extended chain polyvinyl alcohol fibers, extended chain polyacrylonitrile fibers, polybenzazole fibers, such as polybenzoxazole (PBO) and polybenzothiazole (PBT) fibers, polytetrafluoroethylene fibers, carbon fibers, graphite fibers, silicon carbide fibers, boron carbide fibers, glass fibers, regenerated fibers, metal fibers, ceramic fibers, graphite fibers, liquid crystal copolyester fibers and other rigid rod fibers such as M5® fibers, as well as fibers formed from copolymers, block polymers and blends of the above materials. However, not all of these fibers types are stretchable and unstretchable fibers would not be suitable for use in embodiments where the braided body is to be stretched.

The following examples serve to illustrate the invention.

Examples 1-5 (Comparative) and Example 6-10 (Inventive)

In Comparative Examples 1-5, four 375 denier UHMW PE fibers, each having a tenacity of 37.5 g/denier, were braided together to form braided bodies with a solid braid construction using a commercially available braiding machine (Herzog QU 2/8-100 from Herzog Maschinenfabrik GmbH) with an adjustable gear set that permitted adjustment of the picks per inch of the braid. Five samples were produced and tested, one each at 25 PPI, 21 PPI, 19 PPI, 18 PPI and 17 PPI as shown in Table 1, with each identified in Table 1 as "Braid A." In Inventive Examples 6-10, five additional braided bodies were produced on the same machine with the same settings, but each braided body was formed with four 375 denier UHMW PE fibers, each having a tenacity of 43.5 g/denier. All of the Braid A and Braid B samples were unfused, none were coated with any oil or resin except for the pre-existing spin finish applied during manufacture of the fibers, and none of the braided bodies were heated or stretched after braiding. The braids of Inventive Examples 6-10 are identified as "Braid B." Each braided body from Examples 1-10 were analyzed to determine their breaking strength (pounds force; lbf.), tenacity (grams/denier; g/d), tensile modulus (g/d), braid denier and Palomar knot strength (lbf.) according to conventional measurement methods.

Example 11 (Comparative) and Example 12 (Inventive)

In Comparative Example 11, six ultra high molecular weight polyethylene fibers having a tenacity of 37.5 g/denier were braided together but were neither heated nor stretched, and the fibers were not fused together. The braid had a Palomar knot strength meeting the requirements of an 80 lb. fishing line. The diameter of the line was measured at 0.6 mm. SEM images of this line are provided in FIGS. 1(A) and 1(B).

In Inventive Example 12, four ultra high molecular weight polyethylene fibers having a tenacity of 43.5 g/denier were braided together but were neither heated nor stretched and the fibers were not fused together. The braid had a Palomar knot strength meeting the requirements of an 80 lb. fishing line, wherein the breaking strength of the raw braid was 90.24 lbs force. The diameter of the line was measured at 0.48 mm. SEM images of this line are provided in FIGS. 2(A) and 2(B).

As noted, the inventive fishing line fabricated with fibers having a tenacity of 43.5 g/denier was 20% thinner than the fishing line fabricated with fibers having a tenacity of 37.5 g/denier, each having a Palomar knot strength meeting the requirements of an 80 lb. fishing line, with only 4 fibers required to reach the same fishing line weight rating compared to six.

Example 13 (Inventive) and Example 14 (Comparative)

Figure 3:
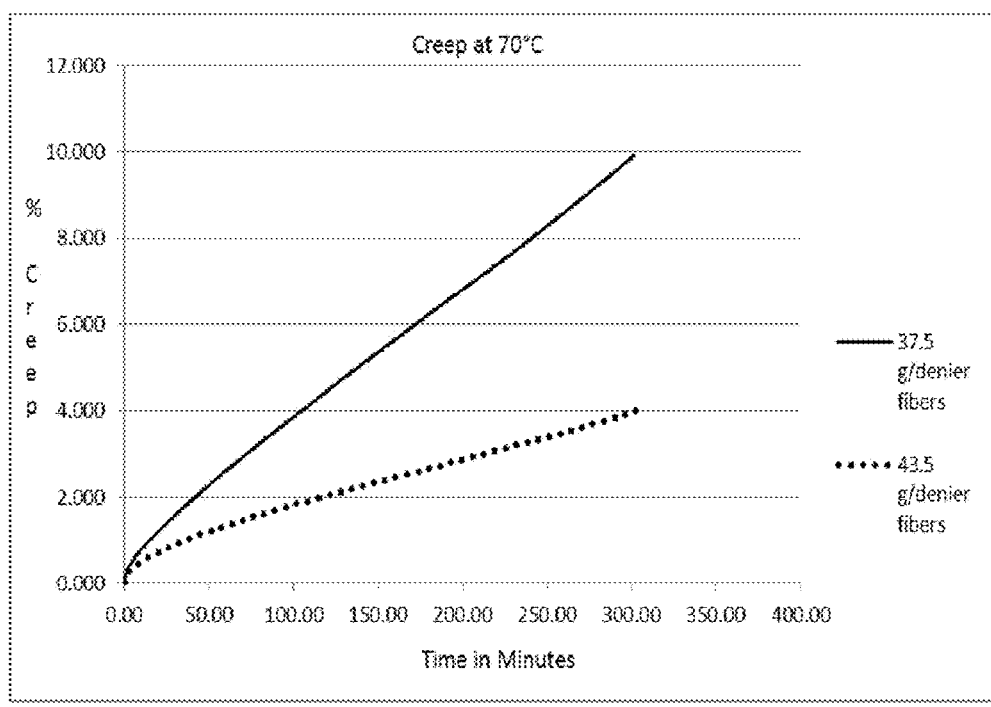
FIG. 3 is a graphical representation of the short term creep of a braided body formed with 4 fibers each having a tenacity of 37.5 g/denier and a braided body formed with 4 fibers each having a tenacity of 43.5 g/denier, wherein creep was measured at 70° C. with each braided body being subjected to a stress equal to 10% of the breaking strength of the braided body for 300 minutes.

The fibers of Example 7 and 8 were tested for short term creep wherein creep was measured at 70° C. with each braided body being subjected to a stress equal to 10% of the breaking strength of the braided body for 300 minutes. The braid formed from four 37.5 g/d fibers had a breaking strength of 69.15 lbs. force and therefore was tested with a 6.9 lb sustained load. The braid formed from the 43.5 g/d fibers had a breaking strength of 90.24 lbs force and therefore was tested with a 9 lb. sustained load. The creep testing results are illustrated in FIG. 3.

Examples 15-19 (Inventive)

Four 375 denier UHMW PE fibers, each having a tenacity of 43.5 g/denier, were braided together to form braided

TABLE 1

|  | 25 PPI | | 21 PPI | | 19 PPI | | 18 PPI | | 17 PPI | |
| --- | --- | --- | --- | --- | --- | --- | --- | --- | --- | --- |
| Braid Type and Ex. # | Braid A (Ex. 1) | Braid B (Ex. 2) | Braid A (Ex. 3) | Braid B (Ex. 4) | Braid A (Ex. 5) | Braid B (Ex. 6) | Braid A (Ex. 7) | Braid B (Ex. 8) | Braid A (Ex. 9) | Braid B (Ex. 10) |
| Breaking Strength (lbf.) | 48.29 | 66.03 | 62.53 | 79.44 | 64.01 | 87.4 | 69.15 | 90.24 | 69.76 | 88.83 |
| Tenacity (g/d) | 12.94 | 16.18 | 16.81 | 20.94 | 17.58 | 24.52 | 19 | 24.35 | 19.19 | 24 |
| Tensile Modulus (g/d) | 31.8 | 32.9 | 60.9 | 64.6 | 68.7 | 106.4 | 92.1 | 99.9 | 123.6 | 98.4 |
| Braid Denier | 1694 | 1853 | 1689 | 1722 | 1653 | 1618 | 1652 | 1683 | 1650 | 1680 |
| Palomar Knot Strength (lbf) | 42.26 | 57.58 | 40.08 | 52.88 | 45.46 | 62.23 | 45.02 | 61.01 | 46.16 | 59.39 |

As illustrated in the table, the braids of each of the Inventive Samples B have significantly better tensile properties relative to Comparative Samples A.

bodies with a solid braid construction using a commercially available braiding machine with an adjustable gear set that permitted adjustment of the picks per inch of the braid (using a Herzog QU 2/8-100 braiding machine). Five braided body samples were produced and tested, one each at the pick counts in picks per inch as shown in Table 2. All of the braided bodies were unfused and unstretched after braiding and none were coated with any oil or resin. Each braided body was tested for % shrinkage at 145 C for 2 minutes according to the method of ASTM D4974-99. The results are identified in Table 2.

TABLE 2

| EX. | PICK COUNT (PPI) | SHRINKAGE % |
|---|---|---|
| 15 | 25 | 2 |
| 16 | 20 | 2.03 |
| 17 | 18.5 | 2.13 |
| 18 | 17.6 | 1.93 |
| 19 | 16.6 | 1.66 |

Examples 20-24 (Comparative)

Four 375 denier UHMW PE fibers, each having a tenacity of 37.5 g/denier, were braided together to form braided bodies with a solid braid construction using a commercially available braiding machine with an adjustable gear set that permitted adjustment of the picks per inch of the braid (using a Herzog QU 2/8-100 braiding machine). Five braided body samples were produced and tested, one each at the pick counts in picks per inch as shown in Table 3. All of the braided bodies were unfused and unstretched after braiding and none were coated with any oil or resin. Each braided body was tested for % shrinkage at 145 C for 2 minutes according to the method of ASTM D4974-99.

TABLE 3

| EX. | PICK COUNT (PPI) | SHRINKAGE % |
|---|---|---|
| 20 | 25 | 2.76 |
| 21 | 21 | 2.96 |
| 22 | 19 | 2.9 |
| 23 | 18 | 2.8 |
| 24 | 16.9 | 3 |

As shown in Tables 2 and 3, the inventive braided bodies fabricated from fibers having tenacities of 43.5 g/denier exhibited significantly less shrinkage than braided bodies fabricated from fibers having tenacities of 37.5 g/denier.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An elongate body comprising a plurality of fibers, wherein said fibers are braided together and form a braided body, wherein all of said fibers forming the braided body are polyolefin fibers, and wherein at least one of said fibers forming the braided body comprises an ultrahigh molecular weight polyolefin fiber having a tenacity of at least 39 g/denier.

2. The elongate body of claim 1 wherein all of the fibers of the braided body are multifilament, ultra high molecular weight polyethylene fibers.

3. The elongate body of claim 2 wherein said multifilament fibers are either twisted or air entangled.

4. The elongate body of claim 2 wherein said multifilament fibers are neither twisted nor air entangled.

5. The elongate body of claim 2 wherein each of the fibers forming the braided body are ultra high molecular weight polyethylene fibers having a tenacity of at least about 43 g/denier and an intrinsic viscosity of greater than about 19 dl/g.

6. The elongate body of claim 1 wherein the braided body has an elongation of about 4.0% or less when the braided body is subjected to a continuous stress equal to 10% of the breaking strength of the braided body for 300 minutes at 70° C.

7. The elongate body of claim 1 wherein the some or all of the fibers of the braided body are multifilament, ultra high molecular weight polyethylene fibers having an intrinsic viscosity of greater than 19 dl/g, and wherein the braided body has a thermal shrinkage as determined by ASTM D4974 at 145° C. of less than 2.5%.

8. The elongate body of claim 7 wherein the braided body has an elongation of less than 1.5% when subjected to a continuous stress equal to 10% of the breaking strength of the braided body for 10,000 minutes at room temperature.

9. The elongate body of claim 1 wherein the braided body has a braid density of at least about 0.5 pick per inch up to 20 picks per inch in length of the braided body.

10. The elongate body of claim 1 wherein the fibers forming the braided body are unfused.

11. The elongate body of claim 1 wherein the fibers forming the braided body each have a denier of from about 30 to about 400.

12. The elongate body of claim 1 wherein said elongate body has a greater breaking strength relative to a comparison elongate body having an identical diameter, wherein the comparison elongate body is equivalent to the elongate body except that all fibers forming the comparison elongate body have a tenacity of less than 39 g/denier.

13. The elongate body of claim 1 wherein the elongate body further comprises a core polyolefin fiber that is at least partially surrounded by the braided body.

14. The elongate body of claim 13 wherein the core fiber comprises a polyolefin fiber having a tenacity of at least 39 g/denier, wherein the braided body and core fiber are fused together.

15. The elongate body of claim 1 wherein the braided body comprises at least four multifilament ultra high molecular weight polyethylene fibers, each having a tenacity of at least about 45 g/denier, a tensile modulus of at least about 1400 and an intrinsic viscosity of greater than about 19 dl/g.

16. A method of making an elongate body comprising the steps of:
  a) providing a plurality of polyolefin fibers, wherein at least one of the polymeric fibers comprises an ultrahigh molecular weight polyolefin fiber having a tenacity of at least 39 g/denier;
  b) optionally coating at least a portion of each fiber with either a thermoplastic resin or an oil;
  c) optionally twisting or entangling the fibers;

d) braiding the polymeric fibers together to form a braided body;
e) optionally stretching said braided body, wherein the braided body is optionally heated during and/or before stretching to a temperature below the melting point of the fibers;
f) optionally fusing together the fibers forming the braided body; and
wherein all of said fibers forming the braided body are polyolefin fibers.

17. The method of claim 16 wherein the fibers forming the braided body are unfused.

18. The method of claim 16 wherein some or all of the fibers of the braided body are multifilament, ultra high molecular weight polyethylene fibers having a tenacity of at least about 43 g/denier.

19. A method of making an elongate body comprising the steps of:

a) providing a plurality of polyolefin fibers, wherein at least one fiber comprises an ultrahigh molecular weight polyolefin fiber having a tenacity of at least 39 g/denier;
b) optionally coating at least a portion of each fiber with either a thermoplastic resin or an oil;
c) optionally twisting or entangling the fibers;
d) braiding the plurality of fibers around a core fiber, thereby forming a braided body around the core fiber;
e) optionally stretching said braided body and core fiber, wherein the braided body and core fiber are optionally heated during and/or before stretching;
f) optionally fusing together the fibers forming the braided body; and
wherein all of said fibers forming the braided body are polyolefin fibers.

* * * * *